United States Patent
Yamada

(10) Patent No.: US 9,130,346 B2
(45) Date of Patent: Sep. 8, 2015

(54) DEVICE, LIGHT SOURCE DEVICE, AND IMAGING APPARATUS USING THE SAME

(71) Applicant: CANON KABUSHIKI KAISHA, Tokyo (JP)

(72) Inventor: Tomohiro Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/670,332

(22) Filed: Nov. 6, 2012

(65) Prior Publication Data

US 2013/0114086 A1    May 9, 2013

(30) Foreign Application Priority Data

Nov. 9, 2011    (JP) .................... PCT/JP2011/075812

(51) Int. Cl.
| | |
|---|---|
| G01B 9/02 | (2006.01) |
| H01S 3/10 | (2006.01) |
| H01S 5/10 | (2006.01) |
| G01N 21/47 | (2006.01) |
| H01S 5/14 | (2006.01) |

(Continued)

(52) U.S. Cl.
CPC .......... *H01S 5/1021* (2013.01); *G01N 21/4795* (2013.01); *H01S 5/141* (2013.01); *G01B 9/02091* (2013.01); *H01S 3/105* (2013.01); *H01S 5/02284* (2013.01)

(58) Field of Classification Search
CPC .......... H01S 5/14; H01S 5/141; H01S 5/142; H01S 5/1021; H01S 5/02284; H01S 3/105

USPC .......... 356/479, 480, 496, 497, 519; 372/20, 372/31, 32, 34, 68, 92, 97
See application file for complete search history.

(56) References Cited

U.S. PATENT DOCUMENTS

| | | | | |
|---|---|---|---|---|
| 4,079,339 A | * | 3/1978 | Kobayashi et al. | ............. 372/97 |
| 4,328,468 A | * | 5/1982 | Krawczak et al. | ............. 372/97 |

(Continued)

FOREIGN PATENT DOCUMENTS

| | | |
|---|---|---|
| JP | 3-75621 A | 3/1991 |
| JP | 9-064439 A | 3/1997 |

(Continued)

OTHER PUBLICATIONS

H. Cai, B. Liu, X. M. Zhang, A. Q. Liu, J. Tamil, T. Bourouina, and Q. X. Zhang, "A micromachined tunable coupled-cavity laser for wide tuning range and high spectral purity", Oct. 13, 2008, Optics Express 16670, vol. 16, No. 21.*

(Continued)

*Primary Examiner* — Michael A Lyons
*Assistant Examiner* — Violeta A Prieto
(74) *Attorney, Agent, or Firm* — Canon USA Inc IP Division

(57) ABSTRACT

A device includes a first resonating cavity and a second resonating cavity. The first resonating cavity includes a first end surface and a second end surface. The first resonating cavity has a first free spectral range. The first free spectral range is a first frequency of a wavelength dependent ripple in a gain of the device that is a function of a first distance between the first end surface and the second end surface. The second resonating cavity includes a third end surface and a fourth end surface. A second distance between the third end surface and the fourth end surface is set such that an amplitude of the wavelength dependent ripple is reduced.

7 Claims, 6 Drawing Sheets

(51) Int. Cl.
  *H01S 3/105* (2006.01)
  *H01S 5/022* (2006.01)

(56) References Cited

U.S. PATENT DOCUMENTS

| | | | | |
|---|---|---|---|---|
| 4,512,021 | A * | 4/1985 | Chenausky et al. | 372/20 |
| 4,550,410 | A * | 10/1985 | Chenausky et al. | 372/97 |
| 4,680,769 | A * | 7/1987 | Miller | 372/50.22 |
| 4,920,541 | A * | 4/1990 | Baumgartner et al. | 372/23 |
| 5,642,375 | A * | 6/1997 | King et al. | 372/97 |
| 5,682,237 | A * | 10/1997 | Belk | 356/478 |
| 5,684,623 | A * | 11/1997 | King et al. | 359/346 |
| 6,700,904 | B2 * | 3/2004 | Asami | 372/20 |
| 7,843,976 | B2 * | 11/2010 | Cable et al. | 372/20 |
| 8,351,474 | B2 * | 1/2013 | Cable et al. | 372/20 |
| 2002/0054614 | A1 * | 5/2002 | Jin | 372/20 |
| 2004/0213306 | A1 * | 10/2004 | Fennema et al. | 372/38.01 |
| 2011/0216789 | A1 * | 9/2011 | Docter et al. | 372/20 |
| 2011/0249271 | A1 * | 10/2011 | Izatt et al. | 356/497 |
| 2011/0304853 | A1 * | 12/2011 | Yamada et al. | 356/479 |
| 2013/0278935 | A1 * | 10/2013 | Yamada | 356/479 |

FOREIGN PATENT DOCUMENTS

| | | |
|---|---|---|
| JP | 2009-244082 A | 10/2009 |
| JP | 2009-252813 A | 10/2009 |
| JP | 2010-272823 A | 12/2010 |
| JP | 2011-142313 A | 7/2011 |
| JP | 2011-187947 A | 9/2011 |
| WO | 2004/021535 A1 | 3/2004 |
| WO | 2005/031320 A1 | 4/2005 |

OTHER PUBLICATIONS

R. Huber, M. Wojtkowski, K. Taira, and J. G. Fujimoto, "Amplified, frequency swept lasers for frequency domain reflectometry and OCT imaging: design and scaling principles", May 2, 2005, Optics Express 3513, vol. 13, No. 9.*

W. T. Tsang, N. A. Olsson, and R. A. Logan, "Highspeed direct singlefrequency modulation with large tuning rate and frequency excursion in cleavedcoupledcavity semiconductor lasers," Applied Physics Letters 42, 650 (1983).*

* cited by examiner

DEVICE, LIGHT SOURCE DEVICE, AND IMAGING APPARATUS USING THE SAME

TECHNICAL FIELD

The present invention relates to an optical gain smoothing and tunable light source device, and an imaging apparatus using the same.

BACKGROUND ART

Various light sources, particularly, laser light sources with a variable oscillation wavelength, have been used in the field of communication networks and in the field of inspection apparatuses.

In the field of communication networks, the demand for high-speed wavelength switching is growing. In the field of inspection apparatuses, the demand for high-speed and wide-range wavelength sweeping, etc., is growing.

Wavelength-variable (swept) light sources in inspection apparatuses have applications in laser spectrometers, dispersion measuring apparatuses, film thickness measuring apparatuses, swept source optical coherence tomography (SS-OCT) apparatuses, and the like.

Optical coherence tomography is an imaging technique which is designed to obtain tomographic images of a specimen using optical interference and which has recently been actively studied in the medical field in order to realize, for example, micron-order spatial resolution and noninvasiveness.

In swept source optical coherence tomography, depth information is obtained using spectral interference without using spectrometers, resulting in low loss in light intensity. Swept source optical coherence tomography is also expected to acquire a high SN ratio image.

Here, in an apparatus that produces an image using interference of light emitted from a light source, such as an optical coherence tomography apparatus, the spectrum of the light emitted from the light source affects an image to be produced, and the image may be affected by the spectral shape.

Under such circumstances, PTL 1 discloses a technique for multiple relay transmission (long-distance relay transmission) using an optical amplification apparatus, in which a reduction in signal bandwidth and the like which are caused by periodical ripples in gain due to reflection in the optical amplification apparatus is prevented. Specifically, it is disclosed that the frequency at which ripples are created in a plurality of optical amplifiers is controlled to cancel the ripples in the respective optical amplifiers.

CITATION LIST

Patent Literature

PTL 1: Japanese Patent Laid-Open No. 3-75621

PTL 1 discloses a technique in which a plurality of gain media are used in the same frequency region and the frequencies of the amplification-factor ripples of the respective gains are made different from one another to average out the amplification-factor ripples. However, this method requires a plurality of gain media in the same frequency region, and therefore does not eliminate amplification-factor ripples for a light source type in which a single gain medium is used in a single frequency region.

Now, a light source device that can be applied in an SS-OCT apparatus is considered. The SS-OCT apparatus obtains the interference of reflectance spectra from an object which is a specimen under inspection while sweeping the wavelength of the light source. Thus, small variations in intensity during the sweeping of the light source and small changes in spectral shape are preferable in view of preventing the occurrence of false signals which may cause noise in an image to be obtained.

Here, a semiconductor optical amplifier (SOA) is considered as an optical gain medium.

According to the study made by the inventor, it has been revealed that if a wavelength-swept laser device is constructed using an SOA, a Fabry-Pérot resonator (optical resonator) is constructed between two end surfaces of the SOA, separately from an optical resonator for amplifying light to be emitted, and the resonator causes inconvenience.

That is, it has been revealed that due to a Fabry-Pérot resonator constructed by the SOA itself, the transmittance periodically increases or decreases with respect to the optical frequency, that is, gain varies with a dependence on wavelength.

In addition, it has been found that this phenomenon causes a change in oscillation strength during the wavelength sweeping operation or a change in spectral shape, thus causing noise in an image to be obtained.

SUMMARY OF INVENTION

An example of the present invention provides a light source device which is a light source device including an optical resonator including an optical gain medium and an optical member which allows light to pass therethrough, wherein a first Fabry-Pérot resonator defined by a first end surface and a second end surface of the optical gain medium has a first transmittance amplitude corresponding to a frequency in an amplification frequency band of the optical gain medium, a second Fabry-Pérot resonator defined by the second end surface of the optical gain medium and a third end surface of the optical member which faces the second end surface has a second transmittance amplitude corresponding to a frequency in the amplification frequency band, and a resonator length of the second Fabry-Pérot resonator is set such that a composite of the first transmittance amplitude and the second transmittance amplitude is smaller than the first transmittance amplitude. An example of the invention is a device including a first resonating cavity and a second resonating cavity. The first resonating cavity includes a first end surface and a second end surface. The first resonating cavity has a first free spectral range. The first free spectral range is a first frequency of a wavelength dependent ripple in a gain of the device that is a function of a first distance between the first end surface and the second end surface. The second resonating cavity includes a third end surface and a fourth end surface. A second distance between the third end surface and the fourth end surface is set such that an amplitude of the wavelength dependent ripple is reduced.

Further features of the present invention will become apparent from the following description of exemplary embodiments with reference to the attached drawings.

DESCRIPTION OF EMBODIMENTS

The present invention is based on the finding obtained by the inventor that the transmittance amplitude of a Fabry-Pérot resonator (optical resonator) defined by a pair of end surfaces of an optical gain medium, which corresponds to a frequency in the amplification frequency band of the optical gain medium, can be canceled out with the transmittance amplitude of a Fabry-Pérot resonator formed by one of the end surfaces of the optical gain medium and an end surface of another optical member.

Embodiments of the present invention will be described in terms of the problems with a light source device of the related art, which were focused on by the inventor of the present invention.

Figure 8A:
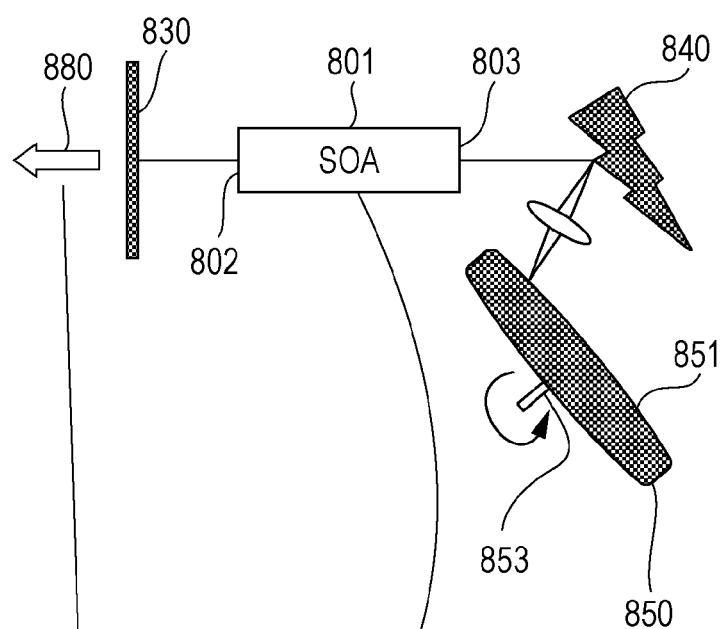
FIGS. 8A and 8B are a schematic diagram and a graph depicting problems with a light source device of the related art, which were focused on by the inventor of the present invention.

FIG. 8A illustrates a typical external resonator type light source device of the related art.

In FIG. 8A, reference numeral 830 denotes one reflecting member (mirror), and reference numeral 850 denotes another reflecting member that rotates about a rotation axis 853 and that has a surface on which a mirror 851 is selectively provided.

Here, an optical resonator is constructed by two reflecting members. The optical resonator includes, as an optical gain medium, a semiconductor optical amplifier (SOA) 801 having a pair of end surfaces 802 and 803, and a diffraction grating 840.

The light generated in the semiconductor optical amplifier 801 and emitted from the end surface 803 is angularly dispersed by the diffraction grating 840 in accordance with the wavelength.

The light angularly dispersed in accordance with the wavelength is reflected by the mirror 851 selectively provided on the surface of the reflecting member 850. The reflected light returns to the semiconductor optical amplifier 801, and is also amplified by the optical resonator (830, 851) and then emitted as emitted light 880.

Here, the oscillation wavelength of the emitted light 880 can be changed (swept) by rotating the reflecting member 850 and moving the position of the mirror 851.

Figure 8B:
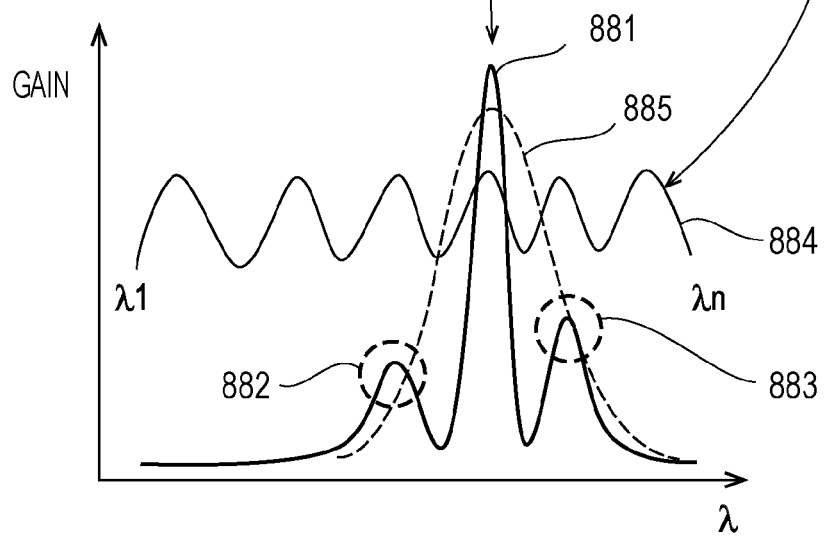

FIG. 8B is a graph illustrating a relationship between the gain of the light 880 emitted from the light source device illustrated in FIG. 8A and the gain of the semiconductor optical amplifier 801 itself.

According to the study made by the inventor, a gain 884 produced by the Fabry-Pérot resonator formed by the pair of end surfaces 802 and 803 of the semiconductor optical amplifier (SOA) 801 varies with the wavelength ($\lambda 1$ to $\lambda n$).

The light to be originally, desirably emitted from the light source device illustrated in FIG. 8A has a spectrum 885 with a single peak.

However, since the gain 884 of the semiconductor optical amplifier 801 itself varies with the wavelength, due to the variation of the gain 884, the originally desirable spectrum 885 becomes a spectrum having peaks of ripples 882 and 883 in addition to a top peak 881. In an example of the invention, a periodic increase and decrease with respect to the optical frequency which is superimposed on the gain spectrum or transmittance spectrum is referred to as a ripple. Because of the variation of the gain 884, the shape of the oscillation spectrum changes with the sweeping of the wavelength.

Further, it has been found that applying the light source device in an OCT apparatus causes a false image (false signal) to be generated on an OCT image due to the variation of the spectral shape along with the sweeping of the wavelength, thus causing noise to appear in a tomographic image obtained by the OCT apparatus.

The present invention has been made in view of the above problems found by the inventor.

An embodiment of the present invention will be described with reference to the drawings.

Figure 1A:
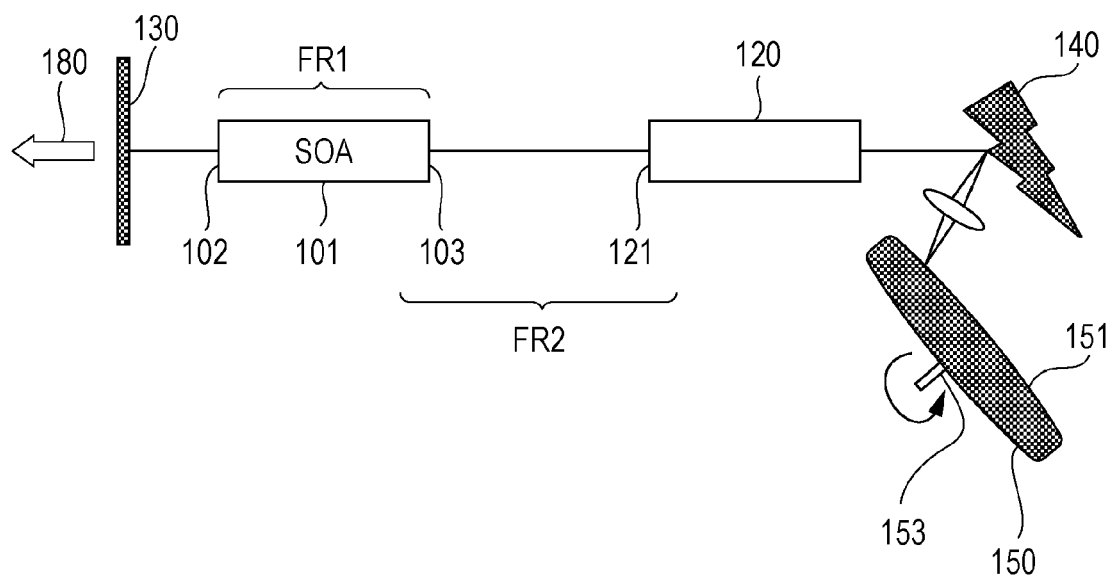
FIGS. 1A and 1B are a schematic diagram and a graph depicting a light source device of an example of the present invention.
Figure 1B:
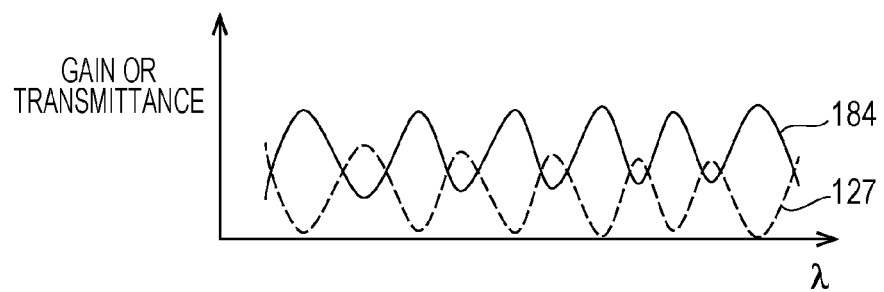

FIGS. 1A and 1B are a schematic diagram and a graph depicting a light source device of an example of the present invention.

In the light source device of an example of the present invention, an optical resonator includes an optical gain medium and an optical member that allows light to pass therethrough, and a Fabry-Pérot resonator formed by an end surface of the optical member and an end surface of the optical gain medium cancels and reduces the variation of the gain of the Fabry-Pérot resonator formed of the optical gain medium itself.

FIG. 1A is a schematic diagram illustrating an example of the light source device of the present invention.

In FIG. 1A, reference numeral 130 denotes one reflecting member (half mirror), and reference numeral 150 denotes another reflecting member that rotates about a rotation axis 153 and that has a surface on which a mirror 151 is selectively provided.

Here, an optical resonator is constructed by two reflecting members (130 and 151), and light is amplified in the optical resonator.

The optical resonator includes an optical member 120 having an end surface 121 that faces an end surface 103 of an optical gain medium 101, which is a feature of an example of the present invention. The optical member 120 is arranged at a specific position in the optical resonator in series with the optical gain medium 101 so as to be adjacent to or close to the optical gain medium 101.

The optical resonator further includes a semiconductor optical amplifier (SOA) 101 having a pair of end surfaces 102 and 103, which serves as an optical gain medium, and a diffraction grating 140. The light generated in the semiconductor optical amplifier 101 and emitted from the end surface 103 passes through the optical member 120 that allows light to pass therethrough, and is angularly dispersed by the diffraction grating 140 in accordance with the wavelength.

The light angularly dispersed in accordance with the wavelength is reflected by the mirror 151 selectively provided on the surface of the reflecting member 150. The reflected light returns to the semiconductor optical amplifier 101, and is also amplified by the optical resonator (130, 151) and then emitted as emitted light 180.

Here, the oscillation wavelength of the emitted light 180 can be changed (swept) by rotating the reflecting member 150 and moving the position of the mirror 151.

The optical member 120 that allows light to pass therethrough is arranged so as to satisfy the following specific conditions.

A first Fabry-Pérot resonator (FR1) defined by the one end surface 102 and the other end surface 103 of the optical gain medium 101 has a first transmittance amplitude corresponding to a frequency in the amplification frequency band of the optical gain medium 101. In addition, a second Fabry-Pérot resonator (FR2) defined by the other end surface of the optical gain medium 101 and the end surface 121 of the optical member 120, which faces the other end surface, has a second transmittance amplitude corresponding to a frequency in the amplification frequency band.

The resonator length of the second Fabry-Pérot resonator is set to a length such that a composite of the first transmittance amplitude and the second transmittance amplitude is smaller than the first transmittance amplitude.

That is, the resonator length of the second Fabry-Pérot resonator (FR2) is set to an appropriate value, thus allowing the variation of the gain (variation of the transmittance, transmittance ripple) with respect to the wavelength (frequency) of the optical gain medium 101 to be canceled out with the variation of the transmittance (transmittance ripple) of the second Fabry-Pérot resonator (FR2).

FIG. 1B is a graph illustrating a relationship between a gain (or transmittance) 184 of the first Fabry-Pérot resonator constructed by the semiconductor optical amplifier 101 itself in the light source device illustrated in FIG. 1A and a transmittance 127 of the second Fabry-Pérot resonator.

In the light source device of an example of the present invention, as illustrated in FIG. 1B, the resonator length of the second Fabry-Pérot resonator is set using the first transmittance amplitude 184 and the second transmittance amplitude 127 so that a composite of them is smaller than the first transmittance amplitude 184.

The light source device of an example of the present invention includes a device in which the frequency at which the first transmittance amplitude takes one of the local maximum value and the local minimum value and the frequency at which the second transmittance amplitude takes the other of the local maximum value and the local minimum value substantially match in a frequency region where the amplification factor in the amplification frequency band of the optical gain medium is maximum.

Here, the term substantially match is used to include the case in which the transmittance ripple at the frequency at which the first transmittance amplitude takes one of the local maximum value and the local minimum value and the transmittance ripple at the frequency at which the second transmittance amplitude takes the other of the local maximum value and the local minimum value are in a range of $1\pi/2$ to $3\pi/2$, and more preferably, in a range of $3\pi/4$ to $5\pi/4$.

A detailed description will now be given with reference to other drawings. In this specification, the same portions even in different drawings are basically given the same numerals in order to avoid a redundant description thereof as much as possible.

Figure 2A:
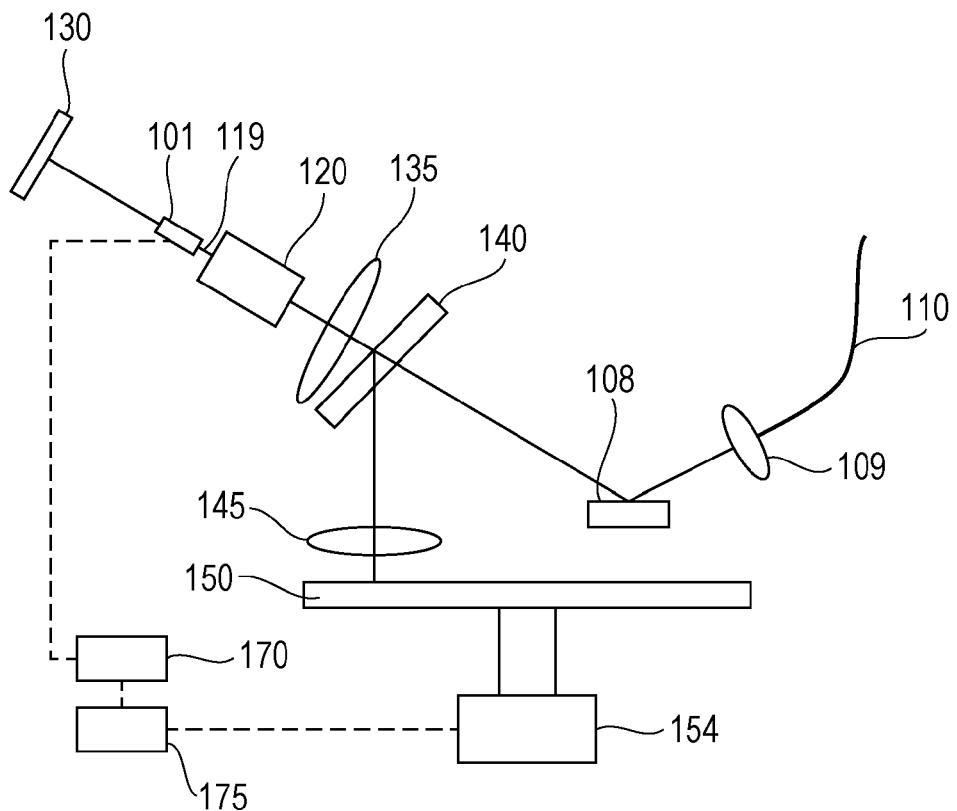
FIG. 2A is a schematic diagram depicting an example of the light source device of the present invention.

FIG. 2A is a schematic diagram illustrating an example of the light source device of the present invention, and is a view of the light source device when viewed laterally.

In the light source device illustrated in FIG. 2A, an optical resonator is constructed using the mirror 130, the semiconductor optical amplifier 101, a collimator lens 135, the diffraction grating 140 serving as a dispersion element, a condenser lens 145, and a rotatable disc 150 having a slit-shaped mirror.

The rotatable disc 150 connected to a control device 154 functions as a reflection-type wavelength selecting element. However, the disc is not limited to the reflection type, and may be a transmission-type wavelength selecting element. In this case, a reflection mirror is arranged downstream of the rotational slit disc. Here, the wavelength selecting element may not necessarily be a disc but may be a polygon like a polygon mirror.

An LD driver 170 connected to a control device 175 is connected to the optical amplifier 101.

The transmitted light from the diffraction grating 140 is reflected by a mirror 108, and is coupled to an optical fiber 110 through a condenser lens 109, so that the output of the light source device is taken out to the outside of the resonator.

In the illustrated example, the optical member 120 that allows light to pass therethrough is implemented using a Fabry-Pérot etalon (hereinafter also referred to as the "etalon"), and the etalon is fixed onto a fine-motion stage (not illustrated), and is arranged adjacent to the semiconductor optical amplifier 101. A Fabry-Pérot resonator 119 is constructed by an end surface of the semiconductor optical amplifier 101 and an end surface of the etalon 120.

The semiconductor optical amplifier 101 has a transmittance ripple in its Fabry-Pérot mode based on internal reflection. The Fabry-Pérot resonator 119 constructed by the end surface of the semiconductor optical amplifier 101 and the end surface of the etalon 120 also has a transmittance ripple.

The resonator length of the Fabry-Pérot resonator 119 is appropriately set, so that the transmittance ripple of the semiconductor optical amplifier 101 itself and the transmittance ripple of the Fabry-Pérot resonator 119 are canceled out with each other in a certain frequency band.

Figure 2B:
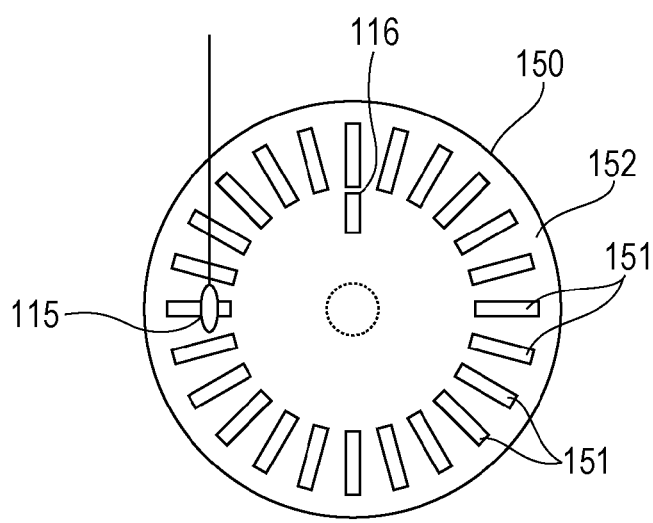
FIG. 2B is a top view of a slit disc of the light source device.

FIG. 2B is a top view of the slit disc 150 of the light source device, and the slit disc 150 has on a top surface thereof a plurality of slit-shaped reflecting portions 151 arranged along the periphery of the disc and a light shielding portion 152. A focusing spot 115 disperses and focuses light in the circumferential direction of the circumferential direction of the slit disc 150 in accordance with the wavelength. In this figure, reference numeral 116 denotes a rotation origin detecting slit, and is used to detect the origin of the rotating slit.

Figure 3:
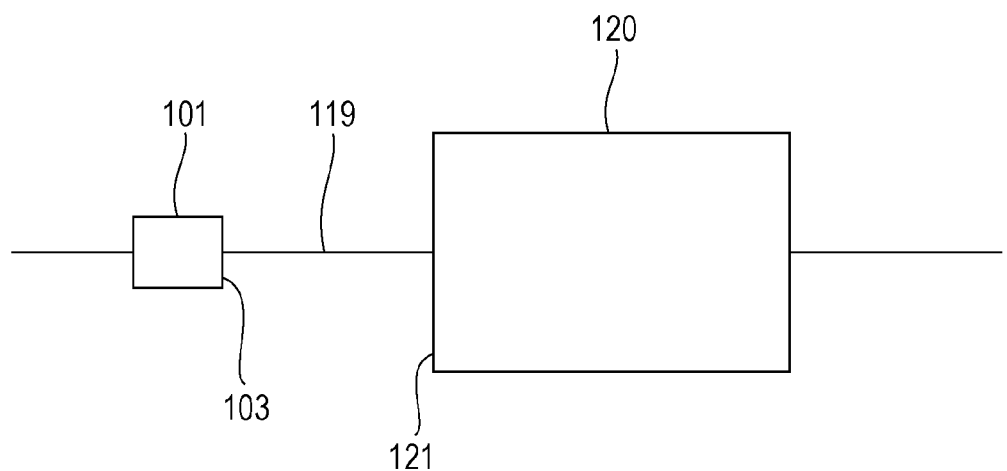
FIG. 3 is a schematic diagram depicting an example of members included in the light source device of the present invention.

FIG. 3 is a diagram illustrating the optical gain medium 101 and the etalon 120 illustrated in FIG. 2A in an enlarged manner. In FIG. 3, the optical gain medium 101 and the etalon 120 are arranged to form the Fabry-Pérot resonator 119 by the end surface 103 of the optical gain medium 101 and the end surface 121 of the etalon 121.

Here, the optical gain medium 101 will be described as a semiconductor optical amplifier (SOA).

Here, an optical path length obtained by multiplying the element length of the optical gain medium 101 by the index of refraction is represented by $L_1$. The resonator length of the Fabry-Pérot resonator 119 is represented by $L'$.

In an example of the present invention, if the following conditional expression, expression (1):

$$L' = L_1 \times \frac{v_0}{v_0 \pm \left(n + \frac{1}{2}\right) \times \frac{c}{2L_1}} \qquad \text{expression (1)}$$

is satisfied, the transmittance ripple of the optical gain medium 101 and the transmittance ripple of the Fabry-Pérot resonator 119 are canceled out at a frequency $v_0$.

Here, in expression (1), the speed of light is represented by c, and an integer is represented by n.

Therefore, by setting the resonator length L' of the Fabry-Pérot resonator 119 with respect to the optical path length $L_1$ of the optical gain medium 101 so as to satisfy the above expression, it is possible to reduce the transmittance ripple of the optical gain medium 101 at the frequency $v_0$.

The conditions for the integer n will now be described.

Because the resonator lengths $L_1$ and L' are different, their FSRs (Free Spectral Ranges) (=c/2 L) have slightly different values. Thus, their transmittance ripples are not superimposed in completely opposite phases in all the frequency bands except $v_0$.

For example, if the peak frequencies of the transmittance ripples in $L_1$ and L' are shifted by just half the FSR of $L_1$ around a certain frequency $v_0$ in the amplification frequency band of the optical gain medium 101, the transmittance ripples are superimposed on one another in phase at the frequency $2 \times v_0$. The transmittance ripples are also superimposed in phase at frequency 0.

Conversely, from the above consideration, the frequency band in which the transmittance ripples in $L_1$ and L' are weakened by each other is a frequency band having a frequency width $v_0$ between about $\frac{1}{2}v_0$ to $3/2v_0$. Therefore, a wavelength-swept light source is preferably used in this frequency band.

Further, in general, if the FSRs of $L_1$ and L' are frequency-shifted by (n+½) times the FSR of $L_1$ at the frequency $v_0$, the frequency bandwidth $\Delta$ in which both are superimposed in opposite phases can be represented by the following expression (2).

The condition where the transmittance ripples in $L_1$ and L' are not at least strengthened by each other in all the regions in the amplification frequency band of the optical gain medium 101 or are superimposed in opposite phases needs to be that the width $\Delta$ is within the amplification frequency band. This condition is given by the following expression (2).

$$\Delta = \left|\frac{1}{2n+1}\right| v_0 \geq 2v_G \quad \text{expression (2)}$$

From the expression (2), the condition satisfied by the n described above is given by the following expression (3).

$$-\frac{1}{2}\left(\frac{v_0}{2v_G} - 1\right) \leq n \leq \frac{1}{2}\left(\frac{v_0}{2v_G} - 1\right) \quad \text{expression (3)}$$

Here, the width of the amplification frequency band of the optical gain medium is represented by $v_G$. In general, the amplification frequency band is set using a frequency bandwidth having an amplification factor that is 3 dB less than the maximum value of the amplification factor.

That is, the interval L' between the end surface 121 of the etalon 120 and the end surface of the optical gain medium 101 is set in accordance with the relational expression given above. Thus, a reduction in the transmittance ripple of the optical gain medium 101 can be prevented.

As described above, superimposing the transmittance ripple of the optical gain medium 101 so as not to be at least strengthened in the amplification frequency band can reduce the change in intensity during the wavelength sweeping operation and the change in instantaneous spectral shape, and makes it possible to stably operate the light source, which is preferable.

In addition, more preferable is the state where the frequency $v_0$ which the transmittance ripples in $L_1$ and L' are superimposed in completely opposite phases is within the amplification frequency band. Since the transmittance ripples are reduced most strongly at the frequency $v_0$, the wavelength sweeping operation around $v_0$ is preferable.

The adjustment method for L' is made possible by, for example, placing at least one of the optical gain medium 101 and the optical member 120 on a fine-motion stage such as a piezo stage and adjusting the interval between them.

In another method, for example, if the optical gain medium 101 is an SOA, $L_1$ can also be changed by adjusting the temperature and the amount of current to finely adjust the index of refraction in the semiconductor element.

The configuration described above is not limited to a system using an etalon. An element that does not have a Fabry-Pérot mode based on internal reflection may also be adopted as an optical element that allows light to pass therethrough. One example is a wedged AR (Anti-Reflection) coated glass plate. In addition, in view of the application to SS-OCT, even though a Fabry-Pérot mode based on internal reflection is present, it is preferable if the frequency of a ripple to be superimposed on the transmittance spectrum is sufficiently high and is outside a frequency band required for SS-OCT imaging.

In an example of the claimed invention, the transmittance amplitude caused by a Fabry-Pérot resonator constructed by two end surfaces of the optical gain medium 101 is reduced using the transmittance amplitude caused by a Fabry-Pérot resonator constructed by an end surface of the optical gain medium 101 and an end surface of the optical member 120 that is arranged adjacent to one end surface of the optical gain medium 101 and that allows light to pass therethrough.

In the light source device, a Fabry-Pérot resonator is constructed by end surfaces of various optical members included in the light source device. For example, in FIG. 2A, Fabry-Pérot resonators are constructed between the mirror 130 and a first end surface of the optical gain medium 101, between a second end surface of the optical gain medium 101 and the rotational disc 150, between the optical member 120 and the rotational disc 150, etc.

However, the resonator lengths of these components can be generally at least 0.5 mm or more. Thus, the frequency of a ripple to be superimposed on the transmittance spectrum can be ignored by setting the frequency to be sufficiently high outside a frequency band required for SS-OCT imaging.

In contrast, the ripple of the Fabry-Pérot resonator caused by the optical gain medium 101 itself is not negligible. In an example of the invention, therefore, the optical member 120 that allows light to pass therethrough is arranged close to or adjacent to an end surface of the optical gain medium 101, thus allowing a reduction in the non-negligible ripple.

The optical member 120 that allows light to pass therethrough can also be formed of an optical gain medium, and, in this case, can be a second optical gain medium.

Here, assuming a wavelength sweeping width $\Delta\lambda$ and an oscillation wavelength $\lambda 0$ in the SS-OCT apparatus, the depth resolution is represented by the following expression (4).

$$\frac{2\ln 2}{\pi} \times \frac{\lambda_0^2}{\Delta\lambda} \quad \text{expression (4)}$$

Therefore, it is necessary to increase the wavelength sweeping width to increase the resolution in the depth direction, and a wavelength swept light source having a wide frequency range is required.

However, it may be difficult to realize an amplification frequency band having a wide frequency range by using a single optical gain medium. Under such circumstances, it is preferable that an overall optical amplification frequency band be developed using a plurality of optical gain media having different amplification frequencies to make the frequency band wider than that in the case of a single amplification medium. The plurality of optical gain media are referred to herein as a first optical gain medium, a second optical gain medium, etc.

When a plurality of optical gain media are used, as in the foregoing discussion, preferably, L' is set so that the transmittance ripple of each optical gain medium and the transmittance ripple of the Fabry-Pérot resonator 119 are not strengthened by each other in the overall optical amplification frequency band. As described above, in the consideration of the transmittance ripples in a plurality of optical gain media being canceled out by the Fabry-Pérot mode based on a plurality of element intervals L', the relational expression between $L_1$ and L' described above can also apply to the relationship between the length $L_2$ of the second optical gain medium and L'. It is to be noted that the length $L_2$ of the second optical gain medium is also equal to the length of a third Fabry-Pérot resonator.

That is, a state is realized in which the transmittance ripple of the first optical gain medium and the transmittance ripple of the Fabry-Pérot resonator 119 are superimposed in opposite phases at a frequency $v_1$ in the overall amplification frequency band formed by a plurality of optical gain media.

In addition, the transmittance ripple of the second optical gain medium and the transmittance ripple of the Fabry-Pérot resonator 119 are superimposed in opposite phases at a frequency $v_2$.

As described above, assuming that $n_1$ and $n_2$ are integers, the following expressions (5) to (8) hold true.

$$L' = L_1 \times \frac{v_1}{v_1 \pm \left(n_1 + \frac{1}{2}\right) \times \frac{c}{2L_1}} \quad \text{expression (5)}$$

$$-\frac{1}{2}\left(\frac{v_1}{2v_G} - 1\right) \le n_1 \le \frac{1}{2}\left(\frac{v_1}{2v_G} - 1\right) \quad \text{expression (6)}$$

$$L' = L_2 \times \frac{v_2}{v_2 \pm \left(n_2 + \frac{1}{2}\right) \times \frac{c}{2L_2}} \quad \text{expression (7)}$$

$$-\frac{1}{2}\left(\frac{v_2}{2v_G} - 1\right) \le n_2 \le \frac{1}{2}\left(\frac{v_2}{2v_G} - 1\right) \quad \text{expression (8)}$$

By realizing a situation that satisfies the expressions given above, it is possible to realize a state where the transmittance ripples in individual gain media are not superimposed so as to be strengthened by one another in the amplification frequency band.

This is preferable because when the frequency range of gain is increased using a plurality of optical gain media, the variation in oscillation strength can be reduced during sweeping and the change in instantaneous spectral shape can also be reduced.

In addition, with the use of this light source, an SS-OCT apparatus with an increased wavelength sweeping band can be constructed, and OCT imaging with low noise and reduced false signals can also be achieved when an OCT signal is acquired.

Here, a description will be made of, as a further preferable example, conditions where the optical amplification frequency band includes frequencies $v_1$ and $v_2$ at which the transmittance ripple of each optical gain medium and the transmittance ripple of a Fabry-Pérot resonator have completely opposite phases.

Here, in expressions, the width of the amplification frequency band of an optical gain medium is represented by $V_G$, having a low-frequency end $v_{GS}$ and a high-frequency end $v_{GE}$. It is further assumed that $n_1$ and $n_2$ are 0. In addition, from the condition where $v_1$ and $v_2$ are $v_{GS}$ or more and $v_{GE}$ or less, the following expressions (9) and (10) are obtained.

That is, the following are yielded:

$$v_{GS} \le \frac{c}{4L_1} \times \frac{L'}{|L_1 - L'|} \le v_{GE} \quad \text{expression (9)}$$

$$v_{GS} \le \frac{c}{4L_2} \times \frac{L'}{|L_2 - L'|} \le v_{GE}. \quad \text{expression (10)}$$

That is, a first optical gain medium and a second optical gain medium have amplification frequency bands in which at least some of the frequencies overlap. Assuming that an overall amplification frequency band of the first optical gain medium and the second optical gain medium has a low-frequency end $v_{GS}$ and a high-frequency end $v_{GE}$, the two expressions given above for $L_1$, L', and $L_2$ are obtained.

In the situation where the expressions given above are satisfied, the variation in oscillation strength and the variation in instantaneous spectral shape are minimized around the frequencies $v_1$ and $v_2$ at which the transmittance ripples have completely opposite phases, which is further preferable for the stable operation of the light source.

While an optical gain medium has been described by taking a semiconductor optical amplifier (SOA) as an example, a semiconductor optical amplifier is preferable because of its compactness and capability of high-speed control.

Materials of a semiconductor optical amplifier may include a general compound semiconductor making up a semiconductor laser, and may specifically include InGaAs-based, InAsP-based, GaAlSb-based, GaAsP-based, AlGaAs-based, GaN-based compound semiconductors. A semiconductor optical amplifier can be selected and used, as desired, from among semiconductor optical amplifiers whose gain center wavelengths are, for example, 840 nm, 1060 nm, 1300 nm, and 1550 nm in accordance with the use of the light source, etc.

Example 1

In this example, the light source device illustrated in FIGS. 2A and 2B was constructed.

FIG. 2A is a view of the light source device of this example when viewed laterally.

In the light source device illustrated in FIG. 2A, an optical resonator is constructed using the mirror 130, the semiconductor optical amplifier 101, the etalon 120, the collimator lens 135, the diffraction grating 140, the condenser lens 145, and the rotatable disc 150 having a slit-shaped mirror. The semiconductor optical amplifier 101 has a gain bandwidth (amplification frequency bandwidth) of 820 nm to 860 nm.

The rotatable slit disc 150 functions as a reflection-type wavelength selecting element. The LD driver 170 connected to the control device 175 is connected to the semiconductor optical amplifier 101.

The transmitted light from the diffraction grating 140 is reflected by the mirror 108, and is coupled to the optical fiber 110 through the condenser lens 109, so that the output of the light source of an example of the present invention is taken out to the outside of the resonator.

The etalon 120 is fixed onto a fine-motion stage (not illustrated), and is arranged adjacent to the semiconductor optical amplifier 101. Here, the Fabry-Pérot resonator 119 is constructed by an end surface of the semiconductor optical amplifier 101 and an end surface of the etalon 120. The optical light path length obtained by multiplying the element length of the semiconductor optical amplifier 101 by the index of refraction is 2.000 mm.

In addition, the fine-motion stage is driven so that the resonator length of the Fabry-Pérot resonator 119 becomes 1.998 mm to arrange the etalon 120. The etalon 120 is wedged by 30 arcminutes at an angle defined by both end surfaces thereof.

Figure 4:
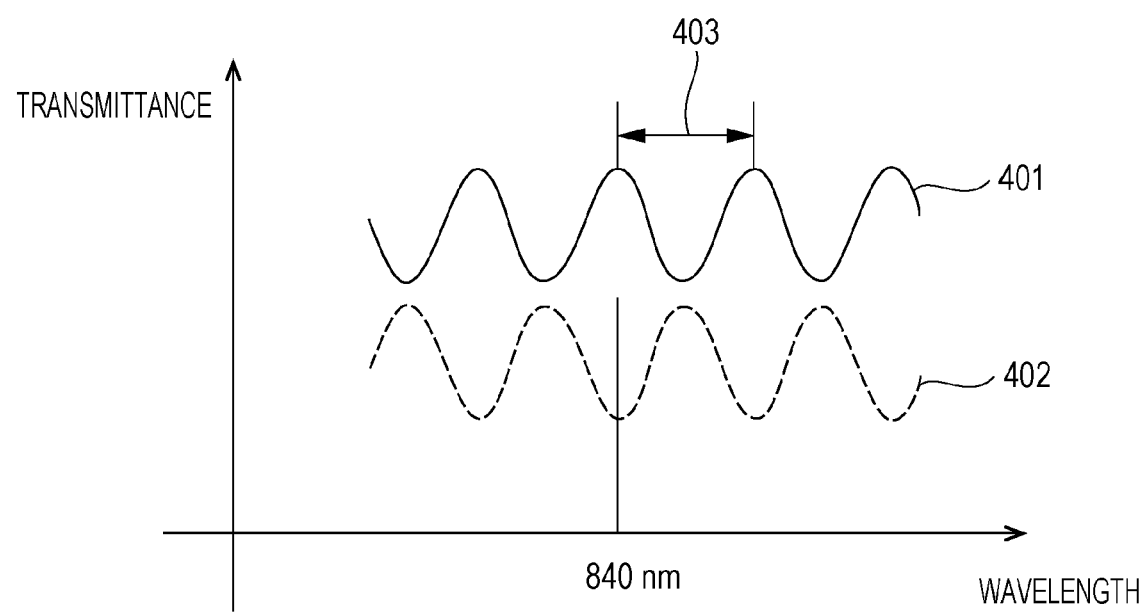
FIG. 4 is a graph illustrating the transmittance of an optical amplifier according to an example of the present invention.

With the above configuration, as illustrated in FIG. 4, a transmittance ripple 401 of the semiconductor optical amplifier 101 itself and a transmittance ripple 402 of the Fabry-Pérot resonator 119 constructed by an end surface of the semiconductor optical amplifier 101 and an end surface of the etalon 120 have opposite phases around a wavelength of 840 nm and overlap.

The length of the Fabry-Pérot resonator 119 is set so that the transmittance ripple 401 of the semiconductor optical amplifier 101 is different from the transmittance ripple 402 of the Fabry-Pérot resonator 119 in such a manner that the peak wavelength of the transmittance ripple 401 is different by half an FSR 403 at a wavelength of 840 nm.

The precision of the length of the Fabry-Pérot resonator 119 required in the condition where the transmittance ripple 401 and the transmittance ripple 402 may not be strengthened by each other even though they do not have completely opposite phases in the gain band is about 400 nm. This precision is a precision that can be adjusted by the drive with a fine-motion stage using a piezo element or the like.

The LD driver 170 is a device for introducing energy to the optical amplifier 101 and controlling its gain. The LD driver 170 is connected to the control device 175, and the control device 175 controls the LD driver 170 and the control device 154 connected to the rotatable slit disc 150. The control device 154 controls the rotational speed of the slit disc 150, supplies power, and performs other operations.

As illustrated in FIG. 2B, the rotatable slit disc 150 has the slit-shaped reflecting portions 151 and the light shielding portion 152. The light shielding portion 152 is composed of chromium oxide having a thickness of 100 nm. The reflecting portions 151 are formed of aluminum having a thickness of 100 nm on a quartz substrate.

As illustrated in FIG. 2B, the focusing spot 115 obtained through the diffraction grating 140 and the condenser lens 145 wavelength-disperses and focuses light in the circumferential direction of the rotational slit disc 150. Then, the origin of the rotating slit is detected by the rotation origin detecting slit 116.

In the light source device of this example, the length of the optical path from the semiconductor optical amplifier 101 to the surface of the rotational slit disc 150 (resonator length) is 50 mm.

The light emitted from the semiconductor optical amplifier 101 is dispersed by the diffraction grating 140, and is focused onto the surface of the rotational slit disc 150. Specifically, light having a wavelength of 820 nm to 860 nm is dispersed over a range having a width of 2.5 mm, and is focused at a different position for each wavelength. The focus position is on the surface of the rotational slit disc 150, and the reflecting portions 151 on the rotational slit disc 150 are moved with respect to the focusing spot to change the wavelength of the reflected light. A wavelength-swept light source is thus obtained.

Here, the condenser lens 145 is a lens having a focal length of 100 mm and a diameter of 5 mm.

In this example, a wavelength-swept light source can be constructed in which the transmittance ripple in the gain band can be reduced with a simple configuration and in which the change in oscillation strength during the wavelength sweeping operation or the change in spectral shape is small.

Example 2

The light source device of this example is a light source device similar to the light source device described in Example 1. The main difference is that a semiconductor optical amplifier 720 in place of the etalon 120 in Example 1 is arranged in series with the semiconductor optical amplifier 101.

Figure 7A:
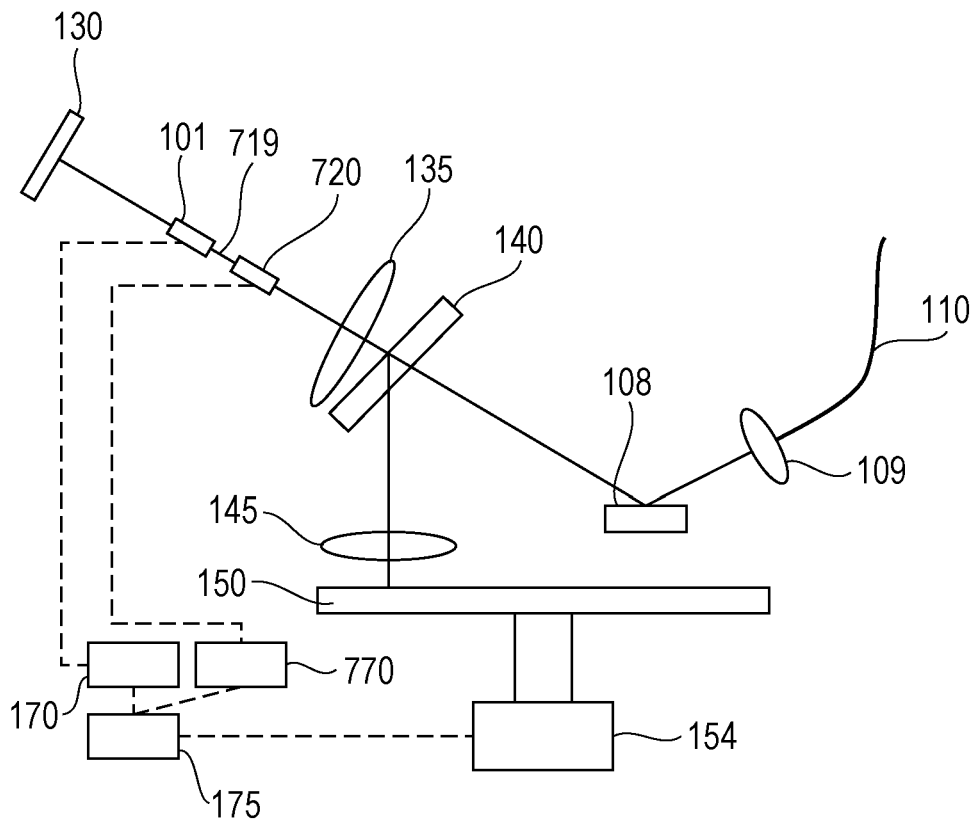
FIG. 7A is a schematic diagram depicting an example of the light source device of the present invention.
Figure 7B:
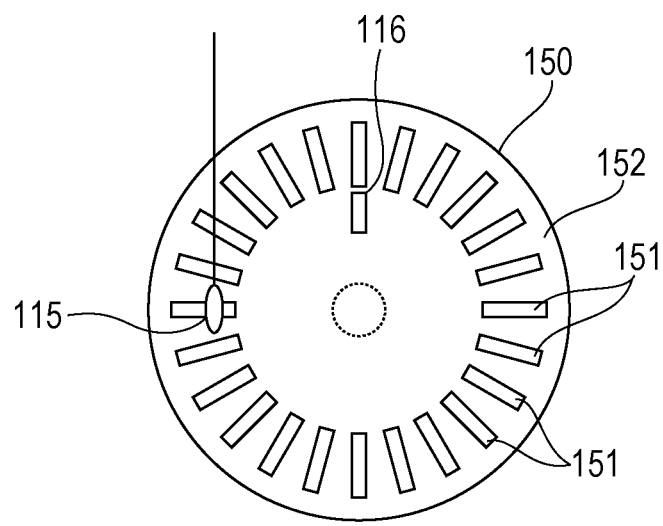
FIG. 7B is a top view of a slit disc of the light source device.

FIGS. 7A and 7B illustrate the light source device of this example. In FIGS. 7A and 7B, the same portions as those included in the light source device of Example 1 are given the same numerals, and a detailed description thereof is thus omitted. A description will be given mainly of the difference.

The gain band of the semiconductor optical amplifier of this example exhibits 800 nm to 880 nm as an overall amplification frequency band of the semiconductor optical amplifier 101 and the semiconductor optical amplifier 720.

The semiconductor optical amplifier 720 is fixed onto a fine-motion stage (not illustrated), and is arranged adjacent to the semiconductor optical amplifier 101. Here, a Fabry-Pérot resonator 719 is constructed by an end surface of the semiconductor optical amplifier 101 and an end surface of the semiconductor optical amplifier 720. The optical light path length obtained by multiplying the element lengths of the semiconductor optical amplifier 101 and a semiconductor optical amplifier 720 by the index of refraction is 2.000 mm.

In addition, the fine-motion stage is driven so that the resonator length of the Fabry-Pérot resonator 719 becomes 1.998 mm to arrange the semiconductor optical amplifier 720.

The condition where the transmittance ripples in each semiconductor optical amplifier and the Fabry-Pérot resonator 719 are not strengthened by each other in the gain band (amplification frequency band) is that the precision of the resonator length of each semiconductor optical amplifier is about 200 nm if the gain band frequency is approximately $\frac{1}{10}$ of the oscillation frequency.

In addition, the difference (precision) that is allowable by the resonator length of each element in order to provide a frequency at which the transmittance ripples in each semiconductor optical amplifier and the Fabry-Pérot resonator 719 are completely canceled out with each other in the gain band frequency is about 20 nm.

It is difficult to modify the resonator length of each element with a precision of 20 nm or less, and the temperature or the amount of current of the semiconductor optical amplifier is changed to slightly change the index of refraction to control the effective element length of each element to finely adjust the FSR of the element, which is also preferable.

In the device of this example, an LD driver 770 is provided in addition to the LD driver 170, and the two drivers individually control the semiconductor optical amplifiers 101 and 720.

The light source device of this example reduces the transmittance ripples in the gain band while realizing a wide frequency range gain using a plurality of optical amplifiers. Therefore, a light source can be constructed in which the change in oscillation strength during the wavelength sweeping operation or the change in spectral shape is small and low noise is created for SS-OCT signals.

Example 3

In this example, an example of an optical coherence tomographic imaging apparatus using the light source of an example of the present invention is illustrated.

Figure 5:
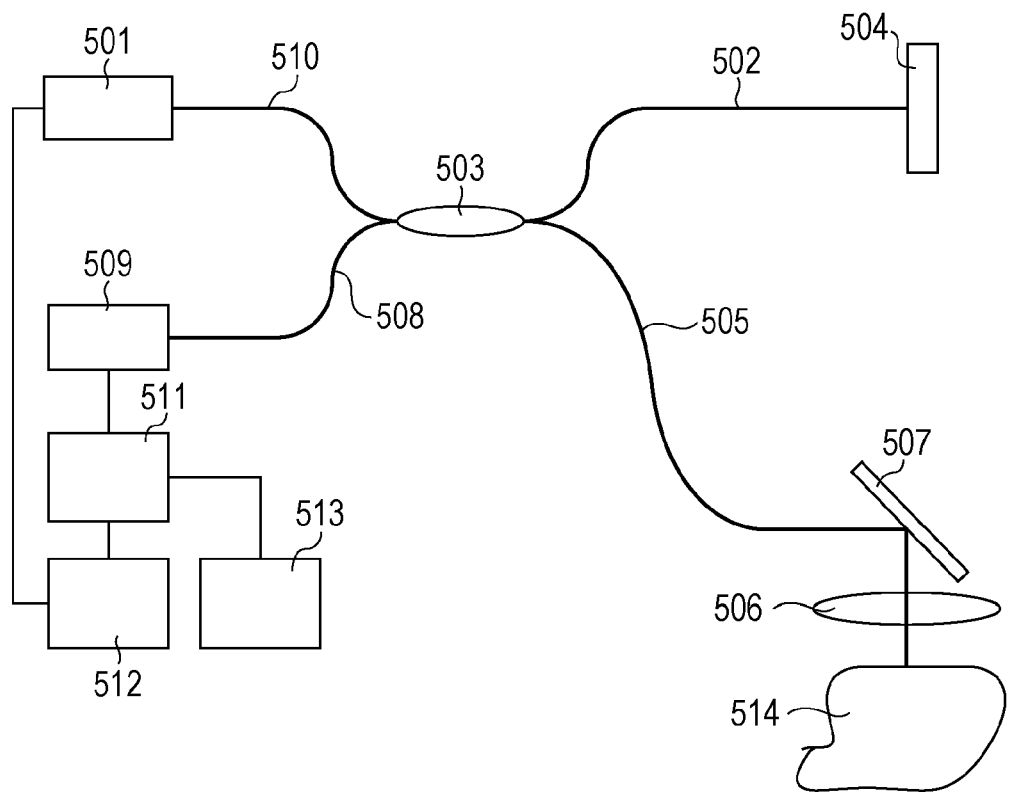
FIG. 5 is a schematic diagram illustrating an example of an OCT apparatus in which the light source device of an example of the present invention is applied.

FIG. 5 is a schematic diagram of an OCT apparatus of this example.

The OCT apparatus illustrated in FIG. 5 basically includes a light source unit (501 etc.), a specimen measurement unit (507 etc.) that irradiates a specimen with light from the light source unit and that transmits the reflected light from the specimen, a reference unit (502 etc.) that irradiates a reference mirror with light and that transmits the reflected light from the reference mirror, an interference unit (503) that causes the two reflected light beams to interfere with each other, an optical detection unit (509 etc.) that detects the interference light obtained by the interference unit, and an image processing unit (511 etc.) that performs image processing (obtain a tomographic image) on the basis of the light detected by the optical detection unit. Each component will be described hereinafter.

The light source unit has a wavelength variable light source 501, and a light source control unit 512 that controls the wavelength variable light source 501, and the wavelength variable light source 501 is connected to a fiber coupler 503 included in the interference unit via a light irradiation optical fiber 510.

The fiber coupler 503 in the interference unit is formed of a single-mode fiber coupler in the wavelength band of the light source, and various fiber couplers are 3-dB couplers.

A reflection mirror 504 is connected to a reference light optical path fiber 502 to form the reference unit, and the fiber 502 is connected to the fiber coupler 503.

The measurement unit includes an inspection light optical path fiber 505, an irradiation focusing optical system 506, and an irradiation position scanning mirror 507, and the inspection light optical path fiber 505 is connected to the fiber coupler 503. In the fiber coupler 503, back scattered light generated from the inside and the surface of an inspection object 514 and the return light from the reference unit interfere with each other to form interference light.

The optical detection unit includes a light receiving fiber 508 and a photodetector 509, and directs the interference light generated in the fiber coupler 503 to the photodetector 509.

The light received at the photodetector 509 is converted into a spectrum signal by the signal processing device 511, and is further subjected to Fourier transform to obtain depth information on the inspection object 514. The obtained depth information is displayed as a tomographic image on an image output monitor 513.

Here, the signal processing device 511 may be formed of a personal computer or the like, and the image output monitor 513 may be formed of a display screen or the like of the personal computer.

A feature of this example is the light source unit, and the light source device of an example of the present invention is used as the wavelength variable light source 501. The oscillation wavelength and intensity of the wavelength variable light source 501 and their changes with time are controlled by the light source control unit 512.

The light source control unit 512 is connected to the signal processing device 511 that also controls a drive signal, etc. for the irradiation position scanning mirror 507, and the wavelength variable light source 501 is controlled in synchronization with the driving of the scanning mirror 507.

For example, if the light source device described in Example 1 or Example 2 is used as the wavelength variable light source 501 of this example, such a light source can reduce the transmittance ripple of a gain medium, and the variation in oscillation strength during wavelength sweeping, the change in instantaneous spectral shape, or the like can be reduced.

Therefore, since the amount of noise in an OCT image is small, a high-SN ratio OCT interference image can be acquired. Thus, a low-reflectance structure or data of weak diffuse light from deep within a body tissue can also be acquired.

Figure 6:
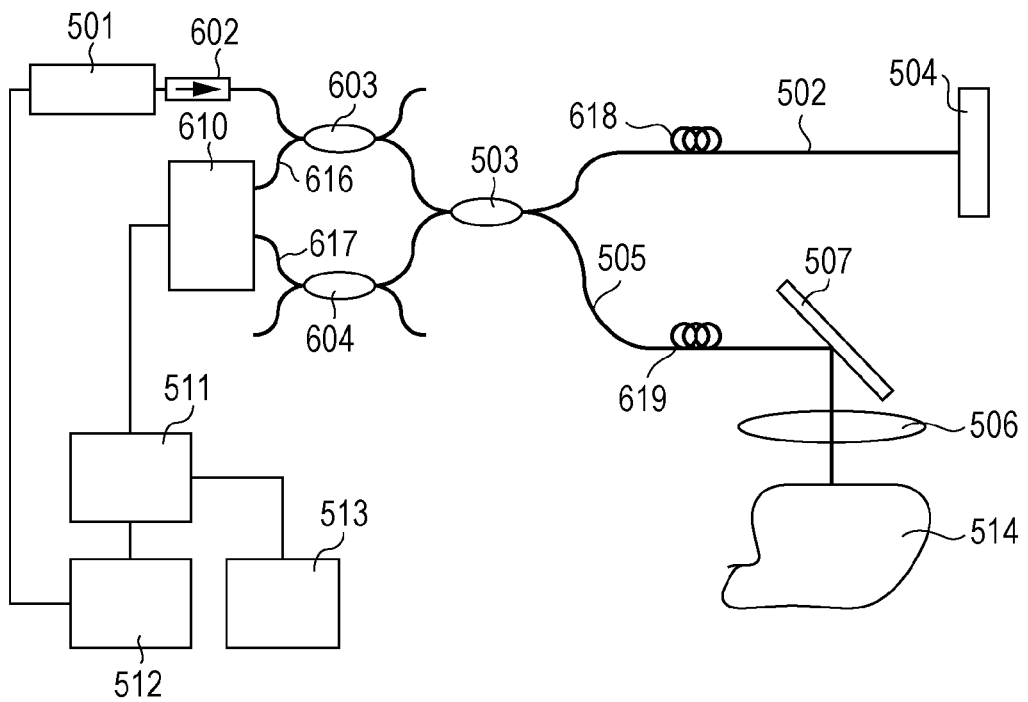
FIG. 6 is a schematic diagram illustrating an example of an OCT apparatus in which the light source device of an example of the present invention is applied.

While an OCT apparatus having a comparatively simple configuration is illustrated in FIG. 5, for example, as illustrated in FIG. 6, the OCT apparatus may be constructed using an optical system for differentially detecting interfering signals.

In the apparatus illustrated in FIG. 6, the same portions as those in the apparatus illustrated in FIG. 5 are given the same numerals.

The apparatus illustrated in FIG. 6 is mainly different from the apparatus illustrated in FIG. 5 in that the apparatus illustrated in FIG. 6 has incorporated therein a balanced photodetector 610 having an optical detector and a differential amplifier and fiber couplers 603 and 604 in place of the photodetector 509 illustrated in FIG. 5.

The balanced photodetector 610 has an end to which the signal processing device 511 is connected, and another end having two 2 terminals. One of the terminals is connected to the fiber coupler 603 via a fiber 616, and the other terminal is connected to the fiber coupler 503 included in a coupling unit via a fiber 617 and the fiber coupler 604.

With the above connection, the optical coherence tomographic imaging apparatus of this example splits the interfering signal having the reflected light from the inspection object 514 and the reflected light from the reference mirror 504 into two parts, and the differential between the one of the two parts and the other is detected.

Light is split into two parts before reaching the balanced photodetector 610 to make the interfering signals have opposite phases. Subtracting one from the other allows only the DC component included in the signal before division to be removed to extract only the interfering signal, which is preferable.

In the figure, reference numeral 602 denotes an isolator, and reference numerals 618 and 619 denote polarization controllers.

It is also possible to sequentially monitor the intensity of emitted light from the light source 501 and to use the resulting data for amplitude correction of an interfering signal. The OCT apparatus of this example is suitably used for tomographic imaging such as ophthalmic imaging, dental imaging, or dermatologic imaging.

The present invention is not limited to the foregoing embodiment, and a variety of changes and medications can be made without departing from the spirit and scope of the present invention. Therefore, the following claims are appended to clearly define the scope of the present invention.

In the light source device of an example of the present invention, the resonator length of the second Fabry-Pérot resonator is set to be a length such that a composite of the second transmittance amplitude of the second Fabry-Pérot resonator and the first transmittance amplitude becomes smaller than the first transmittance amplitude, thus enabling the first transmittance amplitude of the first Fabry-Pérot resonator to be canceled and reduced.

Therefore, the change in oscillation strength during the wavelength sweeping operation or the change in spectral shape is reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Patent Application No. PCT/JP2011/075812, filed Nov. 9, 2011, which is hereby incorporated by reference herein in its entirety.

INDUSTRIAL APPLICABILITY

The present invention can be used in various industrial fields such as the field of communication networks and in the field of inspection apparatuses in which a laser light source is applied.

The invention claimed is:

1. A device comprising:
an optical resonator including an optical gain medium and an optical member which allows light to pass therethrough:
a first Fabry-Pérot resonator constructed by an end and another end of the optical gain medium; and
a second Fabry-Pérot resonator constructed by the another end of the optical gain medium and an end of the optical member facing the another end of the optical gain medium,
wherein the first Fabry-Pérot resonator provides a first ripple to an oscillation spectrum of the optical resonator,
wherein the second Fabry-Pérot resonator provides a second ripple to the oscillation spectrum of the optical resonator,
wherein a resonator length of the second Fabry-Pérot resonator is set such that an amplitude of a sum of the first ripple and the second ripple is smaller than an amplitude of the first ripple at least at one of wavelengths in an amplification frequency band of the optical gain medium, and
wherein another end of the optical member has an anti reflection coating.

2. The device according to claim 1, wherein the optical gain medium and the optical member are arranged adjacent to each other.

3. The device according to claim 1, wherein assuming that at least one frequency in the gain band of the optical gain medium is represented by $v_0$, a length of the first Fabry-Pérot resonator is represented by $L_1$, an integer is represented by n, and the speed of light is represented by c, a length L' of the second Fabry-Pérot resonator satisfies the following expression $$L' = L_1 \times \frac{v_0}{v_0 \pm \left(n + \frac{1}{2}\right) \times \frac{c}{2L_1}},$$

where assuming that a width of the amplification frequency band is represented by $v_G$, n satisfies the following expression $$-\frac{1}{2}\left(\frac{v_0}{2v_G} - 1\right) \le n \le \frac{1}{2}\left(\frac{v_0}{2v_G} - 1\right).$$

4. The device according to claim 1, wherein the optical member is formed of a second optical gain medium.

5. The device according to claim 4, wherein assuming that a length of the first Fabry-Pérot resonator is represented by $L_1$, a length of the second Fabry-Pérot resonator is represented by L', and a length of a third Fabry-Pérot resonator defined by an end surface of the second optical gain medium and another end surface of the second optical gain medium is represented by $L_2$,
the first optical gain medium and the second optical gain medium having amplification frequency bandwidths in which at least some of the frequencies overlap, and assuming that an overall amplification frequency band for the first optical gain medium and the second optical gain medium has a low-frequency end $v_{GS}$ and a high-frequency end $v_{GE}$, $L_1$, L', and $L_2$ satisfy the following two expressions $$v_{GS} \le \frac{c}{4L_1} \times \frac{L'}{|L_1 - L'|} \le v_{GE}$$

$$v_{GS} \le \frac{c}{4L_2} \times \frac{L'}{|L_2 - L'|} \le v_{GE}.$$

6. An optical coherence tomographic imaging apparatus comprising:
a light source unit that uses the device according to claim 1;
a specimen measurement unit that irradiates a specimen with light from the light source unit and that transmits reflected light from the specimen;
a reference unit that irradiates a reference mirror with light from the light source unit and that transmits reflected light from the reference mirror;
an interference unit that causes the reflected light from the specimen measurement unit and the reflected light from the reference unit to interfere with each other;
an optical detection unit that detects interference light from the interference unit; and
an image processing unit that obtains a tomographic image of the specimen on the basis of the light detected by the optical detection unit.

7. The device according to claim 1, wherein the anti reflection coating is wedged.

* * * * *